United States Patent [19]
Wasserman

[11] Patent Number: 5,260,779
[45] Date of Patent: Nov. 9, 1993

[54] METHOD AND APPARATUS FOR INSPECTING A PRINTED CIRCUIT BOARD

[75] Inventor: Harold Wasserman, Belle Mead, N.J.

[73] Assignee: Control Automation, Inc., Princeton, N.J.

[21] Appl. No.: 839,831

[22] Filed: Feb. 21, 1992

[51] Int. Cl.⁵ .................................................. H04N 7/18
[52] U.S. Cl. ...................................... 358/93; 358/101; 382/8
[58] Field of Search ................. 358/93, 101, 106, 107; 382/8

[56] References Cited

U.S. PATENT DOCUMENTS 4,970,597  11/1990  Shepard .................................. 358/93
5,060,065  10/1991  Wasserman ........................... 358/101

*Primary Examiner*—Howard W. Britton
*Attorney, Agent, or Firm*—Weiser & Associates

[57] ABSTRACT

A method and apparatus for inspecting articles such as printed circuit boards doubles the transport rate for the article under inspection, and modifies the manner in which acquired video images are processed to account for this change in rate. Primarily, this involves two modifications to existing video processing systems including a change in synchronization for obtaining the frames which are to be processed, and a selective exposure (i.e., shuttering) of the video cameras to the images which are to be acquired in order to avoid the acquisition of plural images in a single frame. Once acquired, the video images are stored and processed making use of techniques which substantially correspond to those previously employed by existing inspection devices of this general type.

28 Claims, 3 Drawing Sheets

METHOD AND APPARATUS FOR INSPECTING A PRINTED CIRCUIT BOARD

BACKGROUND OF THE INVENTION

This invention relates generally to systems for inspecting printed circuit boards, and more particularly, to an improved system for analyzing successive viewing fields at an increased rate.

As is well known to persons skilled in the art, a printed circuit board is used for mounting and electrically interconnecting electrical components in a predetermined manner. To the extent possible, such printed circuit boards are constructed mechanically, using automated assembly machines which operate to reduce the often prohibitive costs of manually assembling a printed circuit board. While reducing overall costs, such automated assembly techniques have been found to give rise to a certain limited number of assembly defects such as incorrect insertions of components, and their leads or pins, as well as defects in the soldering procedures which then follow.

Originally, steps were taken to locate assembly errors of this general type through a visual inspection of each printed circuit board at a desired stage of the manufacturing process, by human operators using the naked eye, or possibly a stereo microscope or the like. However, since this procedure was found to be extremely tedious and inaccurate, as well as a relatively expensive process, steps were taken to develop automated systems for inspecting printed circuit boards, to replace such visual inspections.

Examples of devices of this general type are the Model 5511, Model 5512, Model 5515, Model 5516 and Model 5517 Printed Circuit Board Inspection Systems which are manufactured by Control Automation Incorporated of Princeton, N.J. These inspection devices generally employ a series of cameras which are mounted within a fixture (an inspection head) adapted for controlled movement relative to a printed circuit board. The inspection head is either sequentially advanced to successive viewing fields (typically one inch by one inch) established along the surface of the printed circuit board then under inspection, or continuously advanced along the surface of the printed circuit board, to acquire images for microprocessor analysis. Any detected defects are in turn reported to the operator, for appropriate correction.

Such devices operate to enhance the accuracy of the inspection process by providing an inspection head which incorporates a series of four angled, orthogonally placed cameras, operated in conjunction with a selectively controllable light source. Through selective control of this series of cameras, and the associated light source, a variety of testing procedures are enabled including a verification of the placement of components (and their leads or pins), both before and after the soldering procedure, as well as a verification of the solder connections which are made.

Initially, such inspections were accomplished by sequentially advancing the inspection head (or the printed circuit board) through successive viewing fields, and by selectively activating the series of cameras and their associated lighting to acquire images for inspection purposes. Later, primarily in order to increase the rate at which circuit board inspections could be accomplished, such inspections were accomplished by continuously advancing the inspection head (or the printed circuit board) through its successive viewing fields, and by selectively strobing the associated lighting system to acquire images for inspection purposes. However, even this enhancement was found to have certain limitations in terms of the rate at which printed circuit boards could be inspected, primarily resulting from limitations associated with the video systems which were employed.

In overall operation, the continuous inspection of a printed circuit board involves scanning of the board in a given direction and at a rate which allows three successive functions to take place including scanning, frame storage and processing. Such techniques, which are often referred to as "pipelining", are primarily limited by the rate at which video images are acquired by the video cameras during the scanning portions of this procedure. The primary reason for this is that conventional video formatting (for the cameras and for display on a monitor) operates within a specified bandwidth, to develop images which are "interlaced" so that changes in the image from frame to frame are less noticeable to the human eye. To this end, the series of lines which conventionally comprise a video image are operated upon in alternating fashion so that a first series of alternating lines (generally referred to as the "odd field") is acquired and/or processed, followed by the acquisition and/or processing of a second series of alternating, interlaced lines (referred to as the "even field"). Resulting from this, the successive (odd/even) fields of a video image are combined to develop a complete frame for subsequent processing, all of which must be accomplished within the operative bandwidth for the system.

Consequently, a period of 33.3 milliseconds is generally required to develop a single frame of video information, for subsequent storage and processing (allowing 16.7 milliseconds for processing the odd and even fields, respectively). The rate at which printed circuit boards can be inspected by existing equipment is correspondingly limited by the rate at which video images can be acquired (i.e., at 33.3 millisecond intervals). For a conventional viewing field (typically one inch by one inch), this limits the rate at which circuit boards can be inspected to approximately 15 inches per second. The reason for this is that the views which are to be acquired by the series of cameras associated with the inspection apparatus are overlapped by 50% (with paired cameras utilizing different lighting modes). As a consequence of this, the inspection head must travel one-half inch (for each pair of cameras) in 33.3 milliseconds, or 15 inches per second.

SUMMARY OF THE INVENTION

It is therefore a primary object of the present invention to provide a method and apparatus for inspecting printed circuit boards at an increased rate.

It is also an object of the present invention to provide a method and apparatus for inspecting printed circuit boards at an increased rate making use of existing video cameras, and video processing systems.

It is also an object of the present invention to provide a method and apparatus for inspecting printed circuit boards at an increased rate which can virtually double the rate of inspection while maintaining the formatting which is necessary for processing and displaying video images.

These and other objects are achieved in accordance with the present invention by providing a method and apparatus for inspecting printed circuit boards which doubles the transport rate for the printed circuit board, and which modifies the manner in which acquired video images are processed to account for this change in rate. Primarily, this involves two modifications to existing video processing systems including a change in synchronization for obtaining the frames which are to be processed, and a selective exposure (i.e., shuttering) of the video cameras to the images which are to be acquired in order to avoid the acquisition of plural images in a single frame. Once acquired, the video images are stored and processed making use of techniques which substantially correspond to those previously employed by existing printed circuit board inspection devices.

For further detail regarding a preferred embodiment method and apparatus produced in accordance with the present invention, reference is made to the detailed description which is provided below, taken in conjunction with the following illustrations.

BRIEF DESCRIPTIONS OF THE DRAWINGS

In the several views provided, like reference numbers denote similar structures.

DETAILED DESCRIPTION OF THE PREFERRED EMBODIMENT

Figure 1:
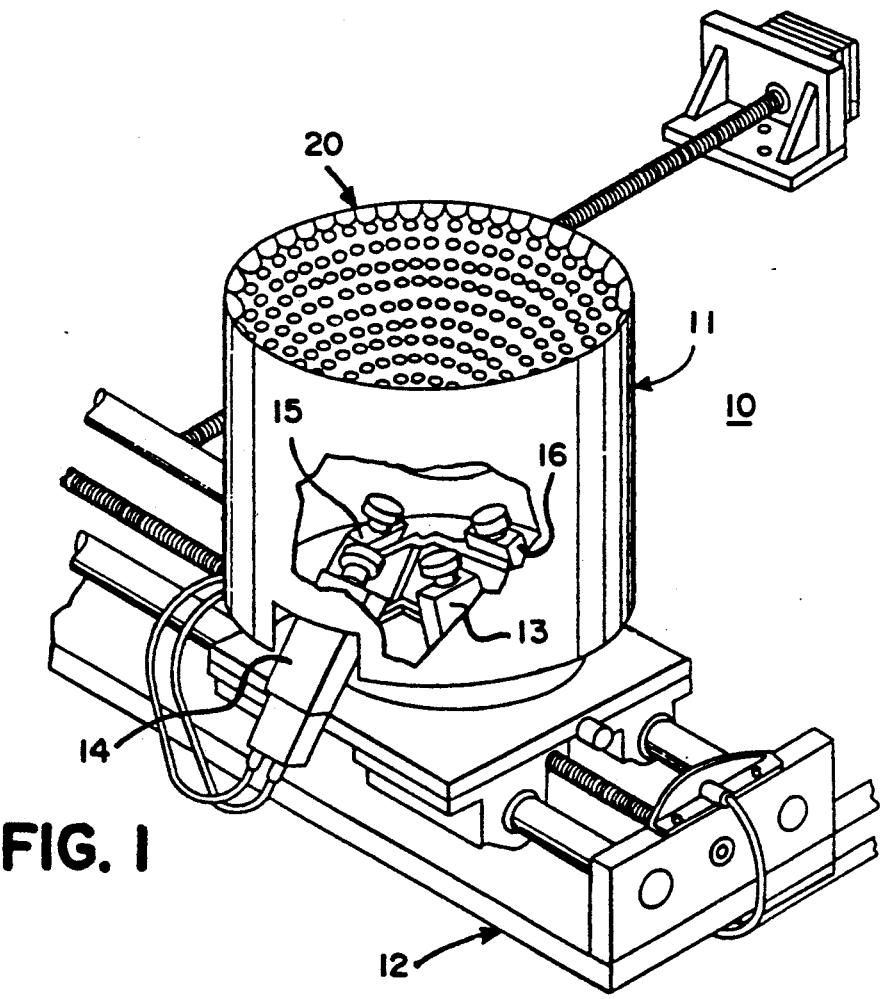
FIG. 1 is an isometric view of the inspection head of a printed circuit board inspection device.

FIG. 1 generally illustrates an apparatus 10 for inspecting printed circuit boards (not shown) in accordance with the present invention. The apparatus 10 generally includes an inspection head 11 which is supported for predetermined movement in a defined plane by an X—Y table (generally designated by the reference number 12), using any of a variety of known servomotor controls. The inspection head 11 further includes a plurality of TV or video cameras 13, 14, 15, 16, and a lighting fixture 20 for selectively illuminating regions on the printed circuit board so that appropriate images may be acquired by the video cameras 13, 14, 15, 16. Further detail regarding the basic construction of the apparatus 10, its various components, and its manner of operation, may be had with reference to U.S. Pat. No. 5,060,065.

Figure 2:
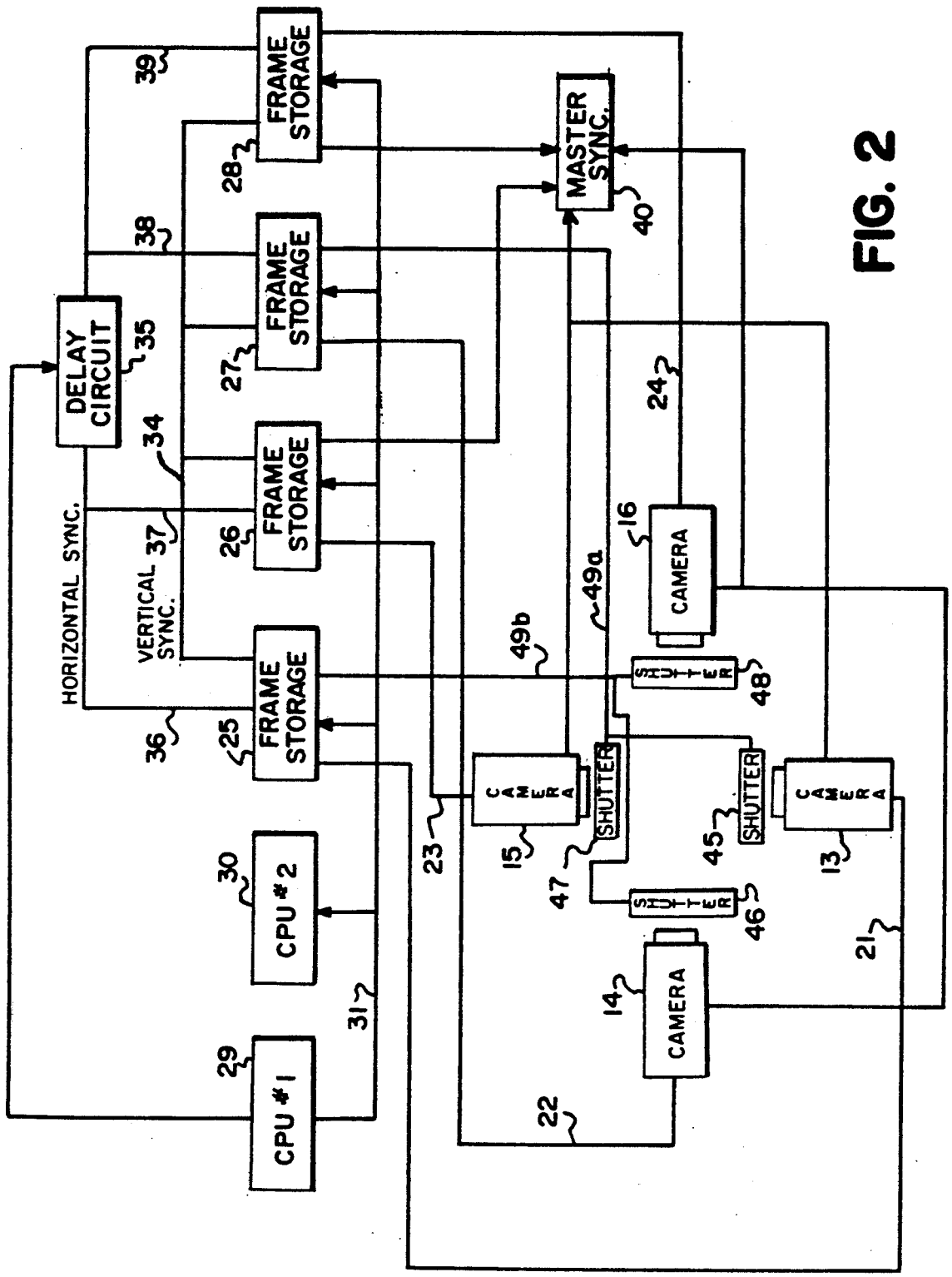
FIG. 2 is a block diagram of a system for acquiring images, and for processing the acquired images, in accordance with the present invention.

Referring now to FIG. 2, images acquired by the cameras 13, 14, 15, 16 are converted to electrical signals (video outputs) which are respectively delivered at 21, 22, 23, 24. The video outputs 21, 22, 23, 24 in turn communicate with a series of frame storage units 25, 26, 27, 28 which operate to receive and temporarily store the video signals for subsequent processing. To this end, the frame storage units 25, 26, 27, 28 communicate with central processing units 29, 30 via an information buss 31. Resulting from this, images acquired by the cameras 13, 14, 15, 16, and stored within the frame storage units 25, 26, 27, 28, can be selectively accessed and processed by the central processing units 29, 30, as desired. Means for implementing these structural components, and for processing the information which is acquired, are known from prior circuit board inspection devices which employ similar structural components and processing techniques. Accordingly, further detail regarding these components is unnecessary to a full understanding of the present invention, other than to describe the interaction of such components with the improvements of the present invention.

In accordance with the present invention, steps are taken to, in essence, double the rate at which circuit boards are inspected by doubling the transport speed for the X—Y table 12, and by modifying the manner in which video images are acquired. Thus, in analyzing typical viewing fields measuring one inch by one inch employing previously known techniques, the X—Y table 12 would conventionally be caused to traverse 0.5 inches in 33.3 milliseconds during operations of the cameras 13, 15, and another 0.5 inches (in another 33.3 milliseconds) during operations of the cameras 14, 16 (which are overlapped by 50%). This produced a transport velocity of approximately 15 inches per second. During this period of time, steps would be taken to acquire an image for storage and subsequent processing, subject to the timing requirements for acquiring video images employing conventional video cameras. In accordance with the present invention, the transport velocity is doubled, to approximately 30 inches per second. However, this has the corresponding effect of reducing the period of time available for acquiring video images by one-half, to approximately 16.7 milliseconds. This then requires certain modification of the overall video processing scheme which is employed.

For example, even though the video intervals established by the method and apparatus of the present invention are reduced by one-half, the video intervals associated with the otherwise conventional video cameras will remain at their normal rate. Resulting from this, the video cameras 13, 14, 15, 16 must now operate in opposing (odd/even) fields. This is because while the cameras 13, 15 are operating in the even field, the cameras 14, 16 will be operating in the odd field, and vice versa. However, it is necessary for the lighting fixture 20 to be strobed while each of the cameras are in their odd field for proper processing of the video signals which are to be produced. Since the cameras 13, 15 and the cameras 14, 16 are now out of phase by 180° (i.e., 16.7 milliseconds apart), steps must therefore be taken to correct this timing. In accordance with the present invention, this is accomplished by delaying the horizontal synchronization for the cameras 14, 16 relative to the cameras 13, 15 by one-half of a horizontal line.

To this end, the horizontal synchronization signal 36 received from the frame storage unit 25 associated with the camera 13, which serves as the master frame storage unit, is delayed prior to application to the frame storage units 27, 28 associated with the cameras 14, 16. This is accomplished by a delay circuit 35 which is configured to establish the one-half horizontal line delay which is desired.

Thus, as shown, the horizontal synchronization signal 36 received from the frame storage unit 25 (master) is coupled with the frame storage unit 26, at 37, maintaining the frame storage units 25, 26 associated with the cameras 13, 15 in synchronization. However, the horizontal synchronization signals 38, 39 for the frame storage units 27, 28 are first subjected to operations of the delay circuit 35, producing the one-half horizontal line delay which is desired for the cameras 14, 16 (which are associated with the frame storage units 27, 28). The position of the horizontal synchronization signals 36, 37, 38, 39 relative to the vertical synchronization signal 34 then determines (identifies) the odd and even fields. Similar modifications are also made to the master synchronization unit 40, which communicates with each of the frame storage units 25, 26, 27, 28, for overall synchronization purposes.

Figure 3:
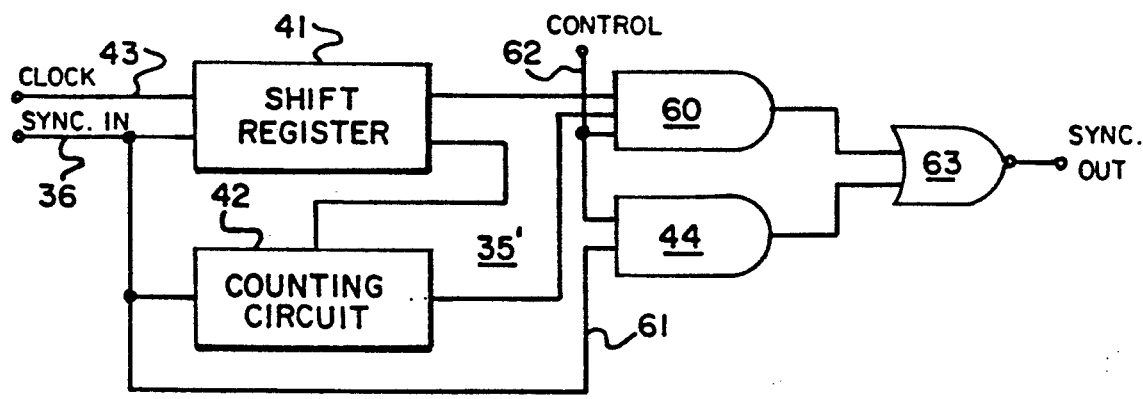
FIG. 3 is a schematic view of a delay circuit for the system which is illustrated in FIG. 2.

The master synchronization unit 40 substantially corresponds to similar units used in existing circuit board inspection devices, modified to accommodate the one-half horizontal line delay developed by the delay circuit 35. Any of a number of known delay circuits may be employed to implement the delay circuit 35. However, a particularly desirable result is achievable by employing the recirculating delay line circuit 35' which is shown in FIG. 3 of the drawings. In this configuration, the horizontal synchronization signal 36 is introduced into a shift register 41 (e.g., a 128-bit shift register) and a counting circuit 42 (e.g., a 3-count shift register). Clock signals 43 for operating the shift register 41 are derived from the horizontal synchronization established for the overall video processing system. Following operations (a first count) of the shift register 41, the counting circuit 42 is advanced, and the shift register 41 is caused to produce a second count. Following this, the counting circuit 42 is again advanced, and the shift register 41 is caused to produce a third count. This, in turn, activates a gating circuit 44, which corresponds to a delay equal to one-half of a horizontal line, as is desired.

Yet another consideration resulting from conventional video formatting is that the acquired image, and the resulting signal, is integrated through interlaced first (odd) and second (even) fields. The acquired images (signals) are output serially, leading with the odd field and followed by the even field. However, each field requires 16.7 milliseconds to be transferred from the camera to its respective frame storage unit. In conventional systems, having the entire 33.3 millisecond period for acquiring a single image, strobing of the lighting fixture 20 did not result in any interaction between the video images (odd/even) acquired by the cameras 13, 14, 15, 16. In strobing the cameras 13, 15, images would also be received by the cameras 14, 16. However, this occurred during a period when operations of the cameras 14, 16 could simply be ignored (blanked), eliminating such secondary images.

Reducing the operative video interval to 16.7 milliseconds results in the production of secondary images which can no longer be ignored, since they are no longer produced during a dormant operating period. Because of this, strobing of the cameras 13, 15 will result in a secondary image in the cameras 14, 16, and vice versa, which will not be automatically eliminated through operations of the cameras. Instead, resulting from the accelerated timing established in accordance with the present invention, these secondary images will interfere with desired operations of the cameras.

For this reason, and in accordance with the present invention, each of the cameras 13, 14, 15, 16 are provided with a shutter 45, 46, 47, 48, respectively, which can be selectively operated to eliminate secondary images received during strobing of the opposing cameras in even fields. Synchronization for the shutters 45, 47 is received from the frame storage unit 27, at 49a, and synchronization for the shutters 46, 48 is received from the frame storage unit 25, at 49b. By closing the shutters of any cameras which are then in their even field, undesirable secondary images are effectively eliminated.

The shutters 45, 46, 47, 48 are preferably liquid crystal shutters, since such shutters are sufficiently fast and resilient to withstand the operations which are required to effectively control the images acquired by the cameras 13, 14, 15, 16. An example of a liquid crystal shutter of this general type is the Model LV050P "light valve" which is manufactured by Displaytech, Inc. of Boulder, Colo. These shutters can operate at speeds in excess of 50 microseconds, a speed which is sufficiently fast to meet the needs which are required of them.

Figure 4:
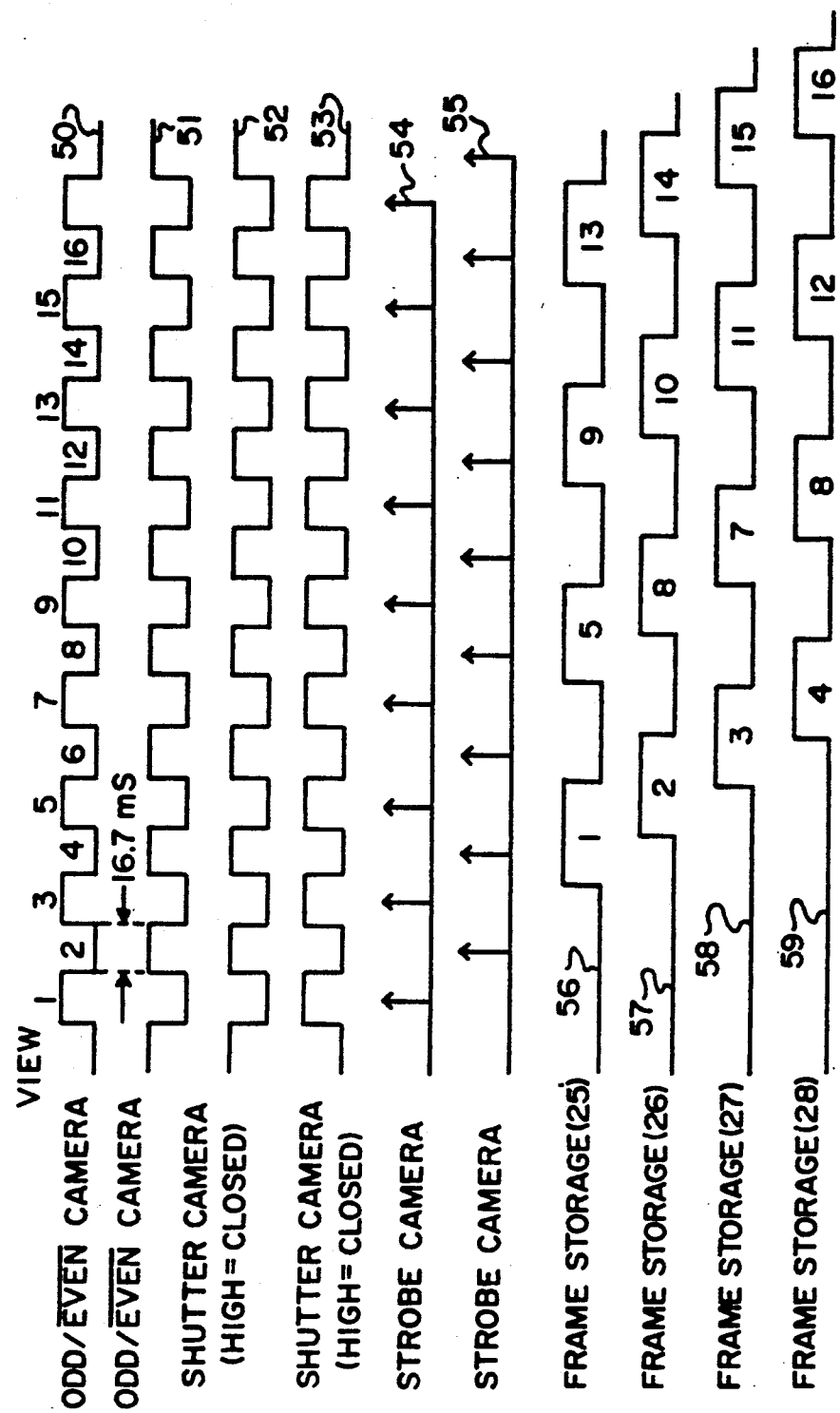
FIG. 4 is a timing diagram for the system which is illustrated in FIG. 2.

In operation, and referring now to FIG. 4 of the drawings, it will be assumed that the circuit board inspection apparatus 10 is operating so that the X—Y table 12 (FIG. 1) is causing the inspection head 11 to traverse a printed circuit board at an increased rate of speed which is achievable in accordance with the present invention (e.g., 29 inches per second). Responsive to synchronization signals received from the frame storage units 25, 26, 27, 28, and the master synchronization unit 40, the cameras 13, 14, 15, 16 will commence the acquisition of images and the conversion of such images to electrical signals 21, 22, 23, 24. Waveforms 50, 51 of FIG. 4 schematically illustrate operation of the video cameras as they progress through this video acquisition process.

To be noted is that the cameras 13, 15 of waveform 50, as well as the cameras 14, 16 of waveform 51, are operated during alternating 16.7 millisecond intervals, as distinguished from the 33.3 millisecond intervals which were previously conventionally utilized. Also to be noted is that the cameras 13, 14, 15, 16 are operated in conjunction with their corresponding shutters 45, 46, 47, 48, according to the waveforms 52, 53 which are illustrated in FIG. 4. The waveform 52 shows operation of the shutters 45, 47 which are associated with the cameras 13, 15, while the waveform 53 shows operation of the shutters 46, 48 which are associated with the cameras 14, 16.

Operations of the video cameras, and their associated shutter mechanisms, are performed in conjunction with strobed operations of the lighting fixture 20, as is illustrated by the waveforms 54, 55 of FIG. 4. It will be noted that strobed operations of the lighting fixture 20 in conjunction with the cameras 13, 15 (waveform 50) occur when the associated shutters 45, 47 are open (waveform 52). Similarly, strobed operations of the lighting fixture 20 in conjunction with the cameras 14, 16 (waveform 51) occur when the associated shutters 46, 48 are open (waveform 53). Although the strobed operations represented by the waveforms 54, 55 are shown to occur substantially midway within the active operational periods which are shown, other timing configurations may also be developed within the 16.7 millisecond "windows" which are established in accordance with the present invention.

Resulting from this, framed images are transferred to the frame storage units 25, 26, 27, 28, storing successive video images represented by the waveforms 56, 57, 58, 59. These images are then accessed by the central processing units 29, 30, for interpretation using techniques which are in and of themselves known, and employed in prior circuit board inspection systems of this general type.

Such processing will continue until the entire surface of a printed circuit board is inspected. Following this, the X—Y table 12, as well as the frame storage units 25, 26, 27, 28, are returned to their initial state, readying them for inspection of the next printed circuit board to be operated upon. During this period of time, the horizontal delay earlier established by the delay circuit 35 is discontinued in order to facilitate operator functions (i.e., user menus, operator interfaces, and video displays on the monitor associated with the printed circuit board inspection system). This is necessary since the desired video images could not otherwise be displayed on a monitor due to the changes in synchronization which are developed by the delay circuit 35.

To this end, and referring again to FIG. 3, a second gating circuit 60 is provided which receives as its input 61 a conventional (without delay) synchronization signal from the apparatus 10. Application of a control signal, at 62, operates to deactivate the gating circuit 44 and to activate the gating circuit 60, removing the delay established by the delay circuit 35 when desired. Signals received from the gating circuits 44, 60 are combined at 63, for subsequent interaction with the remainder of the printed circuit board inspection apparatus 10 as desired.

It will therefore be understood that various changes in the details, materials and arrangement of parts which have been herein described and illustrated in order to explain the nature of this invention may be made by those skilled in the art within the principle and scope of the invention as expressed in the following claims. For example, although the above description of a preferred embodiment device addresses the inspection of printed circuit boards, the method and apparatus of the present invention may similarly be employed to inspect other articles, such as manufactured parts or the like. Other applications will become readily apparent to the skilled artisan.

What is claimed is:

1. An apparatus for inspecting an article, comprising:
a head for inspecting regions defined on the article;
a plurality of cameras coupled with the inspecting head, wherein at least a first one of the cameras is operated responsive to a first synchronization signal and at least a second one of the cameras is operated responsive to a second synchronization signal, and wherein the second synchronization signal is delayed relative to the first synchronization signal;
means for selectively illuminating the regions defined on the article; and
means for selectively exposing the plurality of cameras to images resulting from selective operations of the illuminating means.

2. The apparatus of claim 1 wherein the inspecting head is adapted for inspection of a plurality of different regions defined on the article.

3. The apparatus of claim 2 wherein the article is a printed circuit board.

4. The apparatus of claim 1 wherein the means for selectively exposing the cameras to images are shutter means coupled with lens portions of the cameras.

5. The apparatus of claim 4 wherein the shutter means are liquid crystal shutters.

6. The apparatus of claim 4 wherein the shutter means are operated responsive to the first and second synchronization signals for operating the cameras.

7. The apparatus of claim 4 wherein the cameras operate in cooperating odd and even fields, wherein the illuminating means is selectively operated in odd fields associated with the cameras, and wherein the shutter means are open in odd fields associated with the cameras and closed in even fields associated with the cameras.

8. The apparatus of claim 1 wherein the inspecting head incorporates four, orthogonally disposed cameras.

9. The apparatus of claim 8 wherein two of the cameras are operated as a first pair, and another two of the cameras are operated as a second pair.

10. The apparatus of claim 9 wherein the pairs of cameras are positioned in opposing, spaced relation to each other.

11. The apparatus of claim 9 wherein the first pair of cameras are operated responsive to the first synchronization signal, and the second pair of cameras are operated responsive to the second synchronization signal.

12. The apparatus of claim 11 wherein the second synchronization signal is delayed relative to the first synchronization signal by an amount of time corresponding to one-half of a frame period.

13. The apparatus of claim 12 wherein the delay is developed by delay circuit means comprising a shift register for producing a plurality of counts, and a counter coupled with the shift register for producing a predetermined number of counts of the shift register, wherein the predetermined number of counts corresponds to the delay to be developed.

14. The apparatus of claim 12 wherein the delay is approximately 16.7 milliseconds.

15. The apparatus of claim 14 wherein the inspecting head is adapted for inspection of a plurality of different regions defined on the article at a rate of approximately 30 inches per second.

16. A method for inspecting an article with an apparatus including a head for inspecting regions defined on the article, and a plurality of cameras coupled with the inspecting head, wherein at least a first one of the cameras is operated responsive to a first synchronization signal, and at least a second one of the cameras is operated responsive to a second synchronization signal, the method comprising the steps of:
delaying the second synchronization signal relative to the first synchronization signal;
selectively illuminating the regions defined on the article; and
selectively exposing the plurality of cameras to images resulting from selective operations of the illuminating means.

17. The method of claim 16 wherein the article is a printed circuit board.

18. The method of claim 16 wherein the selective exposure of the cameras to images is accomplished by shutter means coupled with lens portions of the cameras.

19. The method of claim 18 which further comprises the step of operating the shutter means responsive to the first and second synchronization signals for operating the cameras.

20. The method of claim 18 which further comprises the steps of operating the cameras in cooperating odd and even fields, illuminating the region defined on the article when the cameras are in the odd field, and opening the shutter means in odd fields associated with the cameras while closing the shutter means in even fields associated with the cameras.

21. The method of claim 16 wherein the inspecting head incorporates four, orthogonally disposed cameras, and wherein the method further includes the steps of operating two of the cameras as a first pair, and another two of the cameras as a second pair.

22. The method of claim 21 wherein the pairs of cameras are positioned in opposing, spaced relation to each other.

23. The method of claim 21 which further includes the steps of operating the first pair of cameras responsive to the first synchronization signal, and operating the second pair of cameras responsive to the second synchronization signal.

24. The method of claim 23 wherein the second synchronization signal is delayed relative to the first synchronization signal by an amount of time corresponding to one-half of a frame period.

25. The method of claim 24 wherein the delay is developed by producing a plurality of counts in a shift register, counting the number of counts produced in the shift register, and signalling completion of the delay following a predetermined number of counts corresponding to the delay to be developed.

26. The method of claim 24 wherein the delay is approximately 16.7 milliseconds.

27. The method of claim 26 which further comprises the step of inspecting a plurality of different regions defined on the article.

28. The method of claim 27 wherein the article is inspected at a rate of approximately 30 inches per second.

* * * * *